United States Patent [19]

Nakahashi

[11] 4,232,933
[45] Nov. 11, 1980

[54] OPTICAL SYSTEM OF COLPOSCOPE

[75] Inventor: Kenichi Nakahashi, Hachioji, Japan

[73] Assignee: Olympus Optical Co., Ltd., Tokyo, Japan

[21] Appl. No.: 3,018

[22] Filed: Jan. 12, 1979

[30] Foreign Application Priority Data

Feb. 17, 1978 [JP] Japan ............................ 53/19124[U]

[51] Int. Cl.³ ............................................. G02B 21/00
[52] U.S. Cl. ........................................ 350/19; 350/32; 350/40; 350/44; 350/91; 354/62; 354/79
[58] Field of Search .................... 350/19, 31, 32, 40, 350/44, 91; 354/62, 79

[56] References Cited

U.S. PATENT DOCUMENTS

| | | | |
|---|---|---|---|
| 3,405,990 | 10/1968 | Nothnagle et al. | 350/91 X |
| 3,994,288 | 11/1976 | Stumpt | 350/19 X |
| 4,009,929 | 3/1977 | Abe et al. | 350/35 |
| 4,009,930 | 3/1977 | Abe et al. | 350/35 |
| 4,067,027 | 1/1978 | Yamazaki | 350/19 X |

*Primary Examiner*—Edward S. Bauer
*Assistant Examiner*—Matthew W. Koren
*Attorney, Agent, or Firm*—Weinstein & Sutton

[57] ABSTRACT

An optical system of colposcope comprises a pair of independent observation optical sub-systems each having a family of objective lenses including a magnification varying optical sub-system, the magnification varying sub-system in one observation sub-system being ganged with the magnification varying sub-system in the other observation sub-system. The optical system also comprises a photographing optical sub-system having a family of objective lenses including a magnification varying optical sub-system which is ganged with the magnification varying sub-systems of the observation sub-systems, and an illumination optical sub-system for illuminating an object being examined. The observation, the photographing and the illumination sub-system are disposed so that their optical axes converge on the object being examined.

12 Claims, 12 Drawing Figures

OPTICAL SYSTEM OF COLPOSCOPE

BACKGROUND OF THE INVENTION

The invention relates to an optical system of colposcope and more particularly, to such an optical system of colposcope including an illumination, an observation and a photographing optical sub-system.

Figure 1:
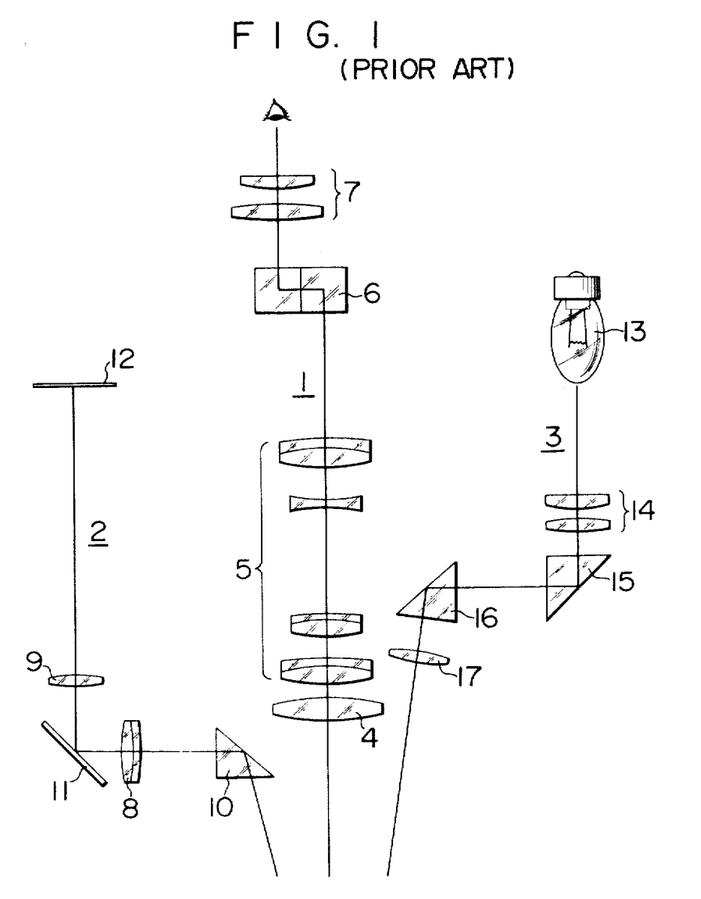
FIGS. 1 and 2 are schematic side elevations of the optical system of conventional colposcopes.

Recently the effectiveness of the colposcopy is recognized in detecting uterocervical cancer in the early stage thereof, and there is a need for a colposcope having an excellent performance. FIG. 1 shows the optical system of a conventional colposcope which includes independent observation optical sub-system 1 and photographing optical sub-system 2. A magnification varying optical sub-system 5 is contained only in the observation sub-system 1. Hence, if the magnification in the sub-system 1 is changed, the magnification in the photographing sub-system 2 remains unchanged, disadvantageously resulting in the lack of coincidence between the extent of observation field and the field being photographed.

The observation optical sub-system 1 includes an objective 4, a magnification varying sub-system 5, Porro prism 6 which converts an inverted image into an erect image, and an eyepiece 7. This constitutes an independent optical sub-system which permits an observation of an object being examined (not shown) which is illuminated by an illumination lamp 13 through an illumination optical sub-system 3. The illumination optical sub-system 3 includes a lens 14 which focusses light from the lamp 13, a pair of prisms 15, 16 which are used to divert the optical path, and a condenser lens 17. The photographing sub-system 2 is also an independent optical sub-system including a prism 10 which diverts the optical path for reflective light from the object being examined, lens 8, reflecting mirror 11 and focussing lens 9, which focusses a light image of the object onto a photographic film 12 which is located at a given position.

Figure 2:
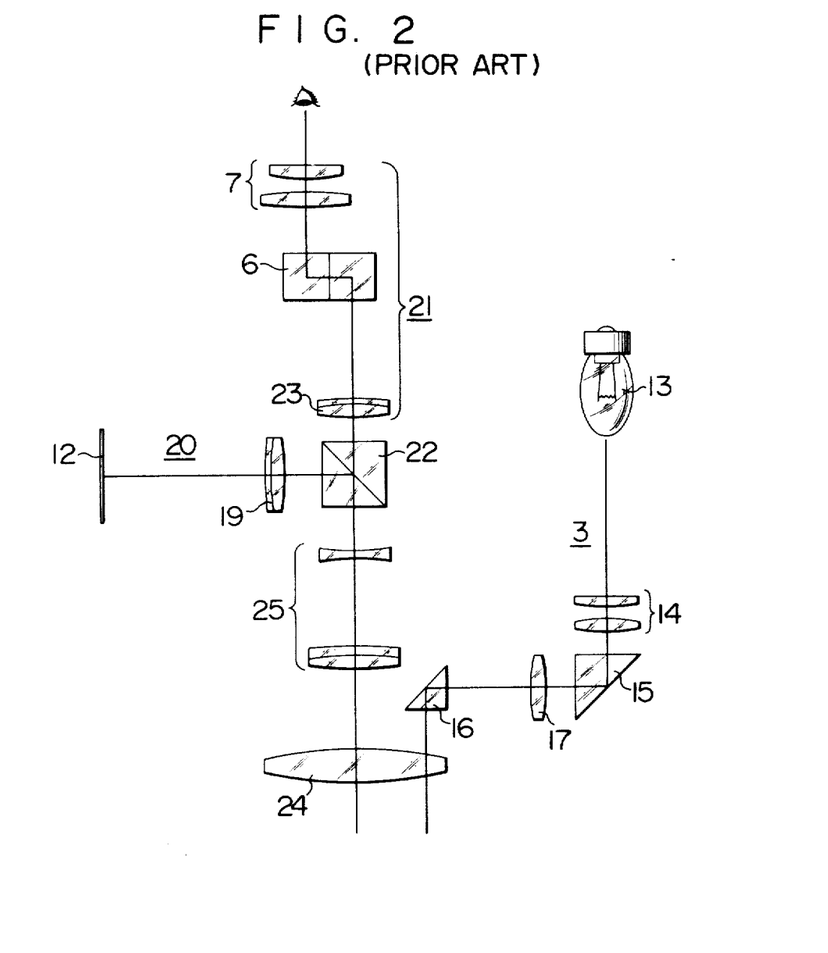

As mentioned previously, when the magnification of the observation sub-system 1 is changed, the extent of the picture taken or picture frame does not coincide with the extent of the field observed. In order to avoid this drawback, there has been proposed another optical system as shown in FIG. 2. In the arrangement of FIG. 2, the object being examined is again illuminated by the lamp 13 through the illumination sub-system 3, and the light from the illuminated object is passed through an objective 24 and through a magnification varying optical sub-system 25 and is then split into two optical paths each associated with an observation sub-system 21 and a photographing sub-system 20. Light incident into the photographing system 20 is focussed by a focussing lens 19 onto the light sensitive surface of the film 12. Light impinging on the observation sub-system 21 is passed through a lens 23 and through Porro prism 6 and eyepiece 7 to reach the eye. With this arrangement, the overall optical system is of a single lens reflex type where the magnification varying sub-system 25 is common to both the observation and the photographing sub-system 21, 20, thus achieving a coincidence between the extent of the field between the observation and photographing sub-systems.

However, the described optical system includes the beam splitter 22 which divides the incident light into two optical paths, thereby tending to cause a substantial reduction in the amount of light fed into both sub-systems 20, 21. As a result, the field of these sub-systems may be darkened. This difficulty may be eliminated by an increased aperture of the optical system, which however disadvantageously results in a larger and more complex arrangement.

SUMMARY OF THE INVENTION

It is an object of the invention to provide an optical system of colposcope which completely eliminates the disadvantages of the prior art.

In accordance with the invention, an observation optical sub-system and a photographing optical sub-system are arranged independently from each other to avoid the problem of insufficient amount of light in the respective sub-systems. A magnification varying optical sub-system is contained in both the observation and the photographing sub-system, and both magnification sub-systems are ganged for operation, thus achieving a complete alignment between the extent of the field observed and that of a picture taken. A binocular vision of an object being examined is enabled by providing a pair of laterally spaced optical sub-systems which constitute together the observation optical sub-system. The optical axes of the various sub-systems are disposed at an angle from each other so that they intersect with each other on the object being examined. This brings forth an advantage that no parallax is produced, despite the arrangement is not of a single lens reflex type. Because the photographing optical sub-system is independent from the observation optical sub-system there is assured a sufficient amount of light, and is possible to dispose in the optical path of the photographing sub-system an optical element such as (a) a movable reflecting mirror which may be moved out of the optical path when a picture is taken or (b) an optical path diverting beam splitter, thereby providing an auxiliary observation path for educational purpose or (c) an output path leading to another photographing apparatus.

DESCRIPTION OF PREFERRED EMBODIMENT

Figure 3:
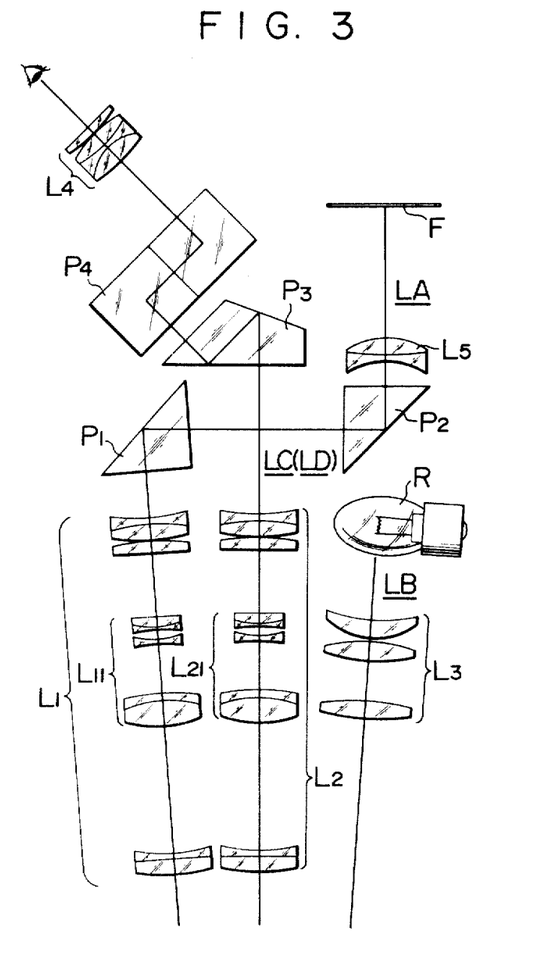
FIG. 3 is a schematic side elevation of the optical system of colposcope according to one embodiment of the invention.
Figure 4:
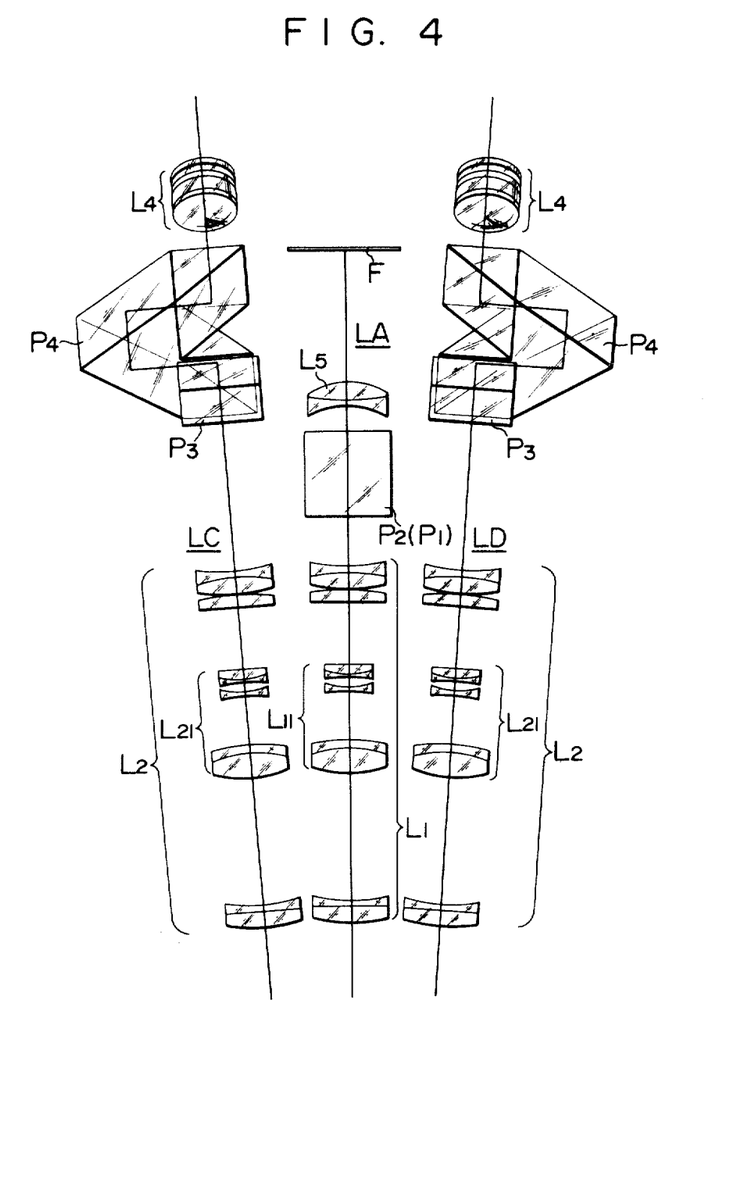
FIG. 4 is a plan view of the optical system shown in FIG. 3 with the illumination optical sub-system being removed.

Referring to FIG. 3, there is shown an optical system of colposcope according to the invention, as viewed from a lateral side. The optical system is shown in plan view in FIG. 4, with the illumination sub-system removed. As illustrated in FIGS. 3 and 4, the optical system includes a photographing optical sub-system LA which comprises a family of objective lenses L1 including magnification varying optical sub-system L11, a pair of first and second prisms P1, P2 which divert the optical path, and a focussing lens L5. The photographing sub-system LA passes a light image from an object being photographed which is illuminated by an illumination optical sub-system LB onto a photographic film F. The illumination sub-system LB comprises a family of condenser lenses L3, and passes light from an illumination lamp R therethrough and directs it onto the object being examined. As viewed from the front of the optical system or from the bottom of FIGS. 3 and 4, the illumination sub-system LB and the family of objective lenses L1 of the photographing sub-system LA are disposed in vertical alignment, as shown in FIG. 5.

Figure 5:
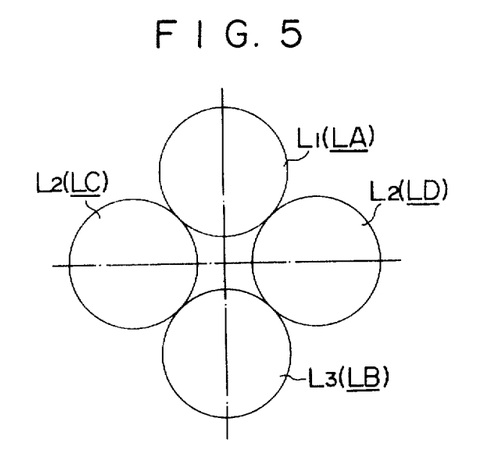
FIG. 5 is a front view illustrating the relative positioning of various optical sub-systems shown in FIG. 3.

The optical system also includes a pair of laterally spaced observation optical sub-systems LC, LD which are independent from each other and which are disposed symmetrically on the opposite lateral sides of the sub-systems LA, LB, as shown in FIG. 5. Each of the observation sub-systems LC, LD comprises a family of objective lenses L2 including a magnification varying optical sub-system L21, an optical path diverting prism P3, a Porro prism P4 which converts an inverted image into an erect image, and an eye-piece L4. It is to be noted that the magnification varying sub-systems L21 contained in the both sub-systems LC, LD are ganged for operation by a mechanism, not shown, which is also connected with the magnification varying sub-system L11 of the photographing sub-system LA for ganged operation. Thus, when it is desired to change a magnification, the magnification varying sub-systems L21, L11 are driven in interlocked relationship.

The family of objective lenses L2 of the observation sub-systems LC, LD inclusive of the magnification varying sub-system L21 has a magnification which is equal to that of the family of objective lenses L1 of the photographing sub-system LA inclusive of the magnification varying subsystem L11. Consequently, if a magnification is changed during the observation, there is maintained a complete coincidence between the extent of field observed and the extent of a picture taken.

The various optical sub-systems LC, LD, LA and LB are disposed in a converging manner or at an angle from each other so that their optical axes intersect with each other on the object being examined. When the observation sub-systems LC, LD and the photographing sub-system LA are disposed so that their optical axes intersect with each other on a point and they are focussed onto a common plane, a misalignment between the field observed and the extent of picture taken or a parallax is removed. The particular angle at which these sub-systems are disposed are chosen in accordance with the distance through which the magnification varying sub-system is moved and the outer diameter of lenses. However, during the use of the colposcope, other instruments which may have a limiting influence upon the field of sight of the optical system are used concurrently, so that the angle is normally limited to less than 6°.

The provision of the pair of observation sub-systems LC, LD in a converging manner permits a binocular vision of the object being examined. The angle which their optical axes form with the perpendicular to the object plane is also limited for the same reason as mentioned above in connection with the observation and photographing sub-systems. It is desirable that the angle be limited below 6° and the angle formed between the optical axes of the both observation sub-systems LC, LD is less than 12°.

Similarly, the purpose of disposing the illumination sub-system LB at an angle is to permit a satisfactory illumination of the object being examined so that reflective light therefrom is effectively incident on both the observation sub-systems LC, LD and the photographing sub-system LA. For the same reason as mentioned above, this angle is also limited to be less than 6°.

In use, light from the lamp R is directed to the object being examined through the condenser lenses L3. Reflective light from the object impinges on the observation sub-systems LC, LD and the photographing sub-system LA. The incident light on the observation sub-systems LC, LD passes through the family of objective lenses L2 including the magnification varying sub-system L21, and is diverted by the prism P3 to follow an optical path which extends upwardly and laterally (see FIG. 3) so as to permit an observation by a viewer without forcing him to assume an unnatural position. Subsequently, the light image is converted into an erect image by the Porro prism P4 to be viewed through the eyepiece L4. On the other hand, the light image of the object being examined which impinges on the photographing sub-system LA passes through the family of objective lenses L1 inclusive of the magnification varying sub-system L11 and has its optical path diverted laterally by the first prism P1 and then upwardly by the second prism P2 to impinge lens L5, which focusses it onto the film F. The provision of the optical path diverting, first and second prisms P1, P2 enables the overall size of the optical system to be reduced in a compact manner by bending the taking path partly so as to be located behind the illumination sub-system LB.

It will be noted that the invention has solved the problem of insufficient amount of light, by providing independent observation systems LC, LD and photographing sub-system LA. Though the arrangement is not of a single lens reflex type, parallax is successfully eliminated by disposing the respective sub-systems so that their optical axes intersect with each other on a point and by employing a magnification varying mechanism in the observation sub-systems LC, LD and the photographing sub-system LA so that the families of objective lenses L1, L2 in the both sub-systems have an equal magnification.

It is necessary for an optical system of colposcope that it has an operating distance on the order of 200 mm in consideration of the depth of the vagina and has a total magnification on the order of 5 or greater in consideration of the thickness of blood vessels. However, if a magnifying system having a magnification greater than unity is used for the family of objective lenses L2, the overall length of the optical system will increase, which is undesirable. To accommodate for this, a reduced optical system having a magnification equal to or less than unity is used for the lens family L2 while a magnifying optical system having a greater magnification is used for the eyepiece L4, thus providing a compact optical system which can be conveniently used. In the embodiment described above, the magnification varying system L11 of the photographing sub-system LA and the magnification varying sub-system L21 of the observation sub-systems LC, LD are constructed by an identical lens system, which is advantageous to simplify the construction of the mechanism which achieves a ganged operation of the magnification varying sub-systems. However, it should be understood that magnification varying sub-systems L11 and L21 of different constructions may be used in the arrangement of the invention with a corresponding change in the ganging mechanism.

Figure 6A:
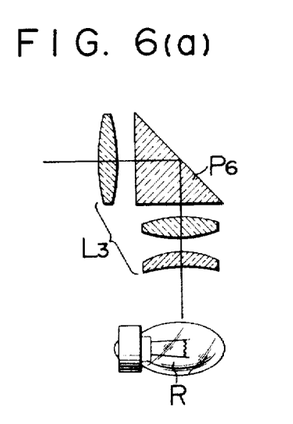
FIGS. 6(a) and (b) are cross sections of other examples of the illumination sub-system.
Figure 6B:
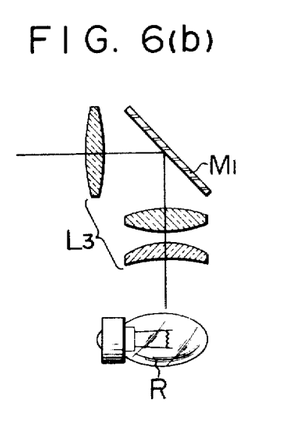
Figure 7A:
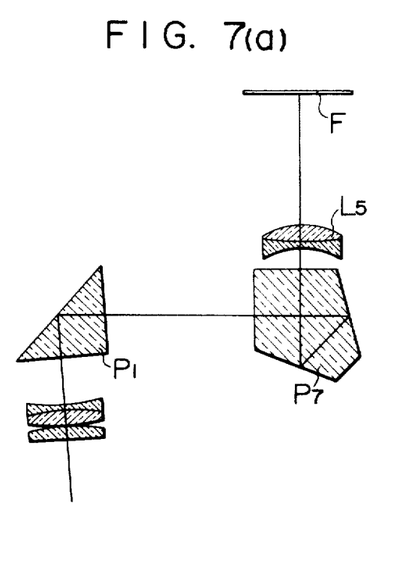
FIGS. 7(a) and (b) are fragmentary cross sections of other examples of the photographing sub-system.
Figure 7B:
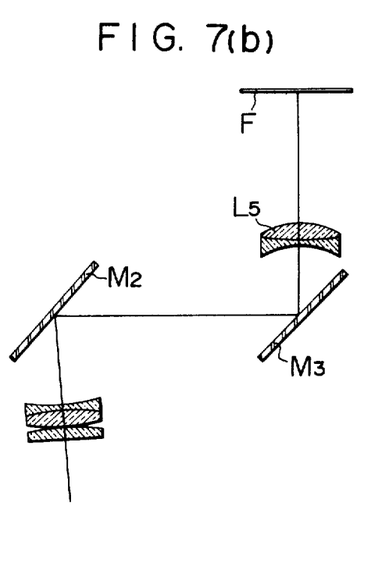

A number of modifications can be made in the embodiment described above. For example, though the illumination sub-system LB is disposed in linear alignment in FIG. 3, a prism P6 or a mirror M1 may be disposed in the optical path to provide a folded path, as illustrated in FIGS. 6(a) and (b). The first and second prisms P1, P2 disposed in the optical path of the photographing sub-system LA which are used to provide a folded optical path to achieve a compact construction of the entire optical system may be replaced by prisms or mirrors of other configurations. In a modification shown in FIG. 7(a), second prism P2 is replaced by a pentaprism P7. In another modification illustrated in FIG. 7(b), both first and second prisms P1, P2 are replaced by reflecting mirrors M2, M3. It will also be noted that an optical path diverting element such as a movable reflecting mirror as may be used in a usual single lens reflex camera or a beam splitter may be disposed in the optical path of the photographing sub-system LA to provide an auxiliary observation path for educational purpose or a film exposure path leading to other photographing apparatus.

Figure 8:
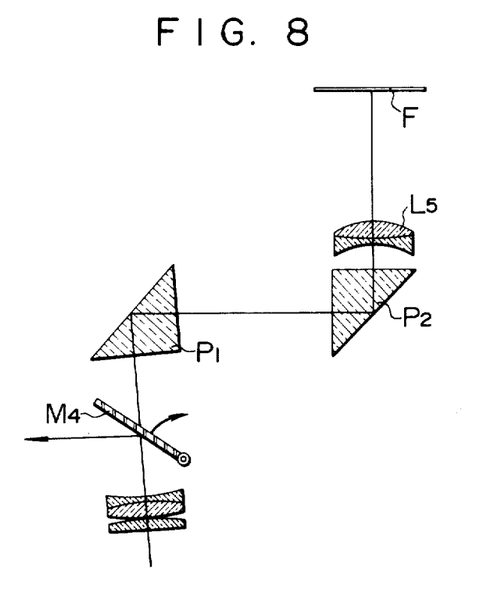
FIGS. 8 to 10 are fragmentary cross sections, showing further examples of the photographing optical sub-system.
Figure 9:
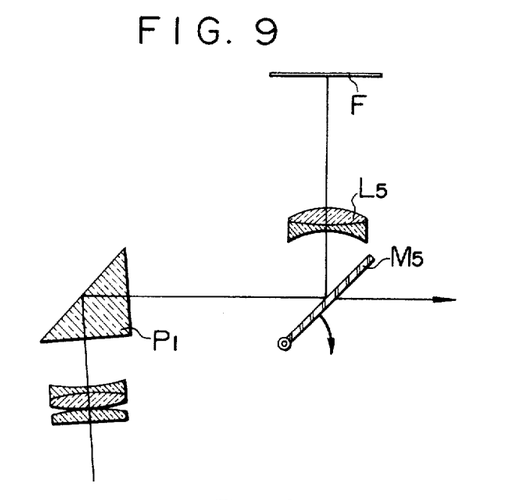
Figure 10:
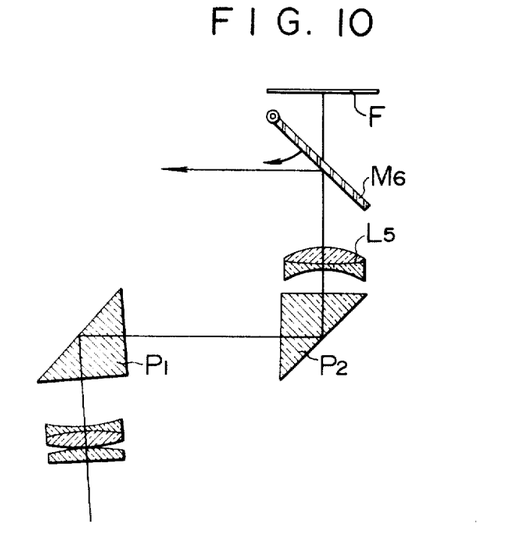

FIG. 8 shows an auxiliary observation path which may be used for educational purpose. Specifically, a movable reflecting mirror M4 which can be moved out of the taking path during the time a picture is to be taken is disposed before the first prism P1 to divert the taking path laterally. However, when a picture is to be taken, the mirror M4 is rotated in the direction indicated by an arrow, thus moving it out of the taking path to establish the original taking path. In FIG. 9, the second prism P2 is replaced by a movable reflecting mirror M5. When a picture is to be taken, flux from the first second prism P1 is reflected to the focussing lens L5 to define a taking path. When it is desired to form an auxiliary observation path for educational purpose, the mirror may be rotated in the direction indicated by an arrow to permit flux from the first prism P1 to be directed laterally out of the normal taking path. In FIG. 10, a movable reflecting mirror M6 is disposed behind the focussing lens L5 to divert the flux from the focussing lens L5 laterally to provide an auxiliary observation path. However, when a picture is to be taken, the mirror M6 is rotated in the direction indicated by an arrow to establish the taking path leading to the film F.

While the prisms P3, P4 are used in the observation optical paths shown in FIGS. 3 and 4 in order to allow a convenient viewing position for purpose of observation and in order to obtain an erect image, these elements can also be replaced by mirrors or prisms having equivalent functions.

What is claimed is:

1. An optical system of colposcope comprising a pair of laterally spaced, independent observation optical sub-systems each having a family of objective lenses including a magnification varying optical sub-system, the magnification varing sub-system in one observation sub-system being ganged with the magnification varying sub-system in the other observation sub-system, a photographing optical sub-system having a family of objective lenses including a magnification varying optical sub-system which is ganged with the magnification varying sub-systems of the observation sub-systems, and an illumination optical sub-system for illuminating an object being examined, the optical axes of the four optical sub-systems being disposed so that they converge on the object being examined.

2. An optical system according to claim 1 in which the family of objective lenses in the observation sub-systems has a magnification which is equal to that of the family of objective lenses in the photographing sub-system.

3. An optical system according to claim 2 in which each of the observation sub-systems comprises the family of objective lenses including the magnification varying optical sub-system, an optical path diverting prism, a Porro prism for converting an inverted image into an erect image, and an eyepiece, the pair of observation sub-systems being symmetrically disposed on the opposite lateral sides of the axes of the illumination and the photographing sub-system.

4. An optical system according to claim 2 in which the photographing sub-system comprises the family of objective lenses including the magnification varying optical sub-system, a pair of optical path diverting, first and second prisms, and a focussing lens.

5. An optical system according to claim 4 in which the first and second prisms each comprise a reflecting mirror.

6. An optical system according to claim 4 in which the photographing sub-system includes a movable reflecting mirror which selectively switches the taking path between an auxiliary observation path and a film exposure path.

7. An optical system of colposcope of claim 1 wherein the angle formed between the optical axes of the observation sub-systems is less than 12°.

8. The optical system of colposcope of claim 7 wherein the optical axes of the observation sub-systems is at an angle less than 6° to the optical axis of the photographing optical sub-system.

9. The optical system of colposcope of claims 1, 7 or 8 wherein the optical axis of said illumination optical sub-system is at an angle of less than 6° to the optical axes of said observation sub-systems.

10. The optical system of colposcope of claim 1 wherein the magnification varying sub-systems of said observation sub-systems and the magnification varying optical sub-system of said photographing optical sub-system each have a magnification equal to or less than unity.

11. The optical system of colposcope of claim 10 wherein the overall magnification of each of said observation sub-systems and said photographing optical sub-system are equal.

12. The optical system of colposcope of claim 11 wherein the family of objective lenses of said observation optical sub-systems and said photographing optical sub-system have a magnification greater than the magnification of said magnification varying sub-systems.

* * * * *